United States Patent
Moro et al.

(10) Patent No.: US 10,925,978 B2
(45) Date of Patent: Feb. 23, 2021

(54) LIQUID COMPOSITION IN THE FORM OF EMULSION OR MICROEMULSION FOR RECTAL ADMINISTRATION CONTAINING AT LEAST ONE DYE, AND ITS USE IN A DIAGNOSTIC ENDOSCOPIC PROCEDURE OF SIGMOID COLON AND/OR RECTUM

(71) Applicant: COSMO TECHNOLOGIES LIMITED, Dublin (IE)

(72) Inventors: Luigi Moro, Cairate (IT); Enrico Frimonti, Nerviano (IT); Luigi Maria Longo, Monza (IT)

(73) Assignee: COSMO TECHNOLOGIES LIMITED, Dublin (IE)

( * ) Notice: Subject to any disclaimer, the term of this patent is extended or adjusted under 35 U.S.C. 154(b) by 124 days.

(21) Appl. No.: 15/115,200

(22) PCT Filed: Jan. 29, 2015

(86) PCT No.: PCT/IB2015/050667
§ 371 (c)(1),
(2) Date: Jul. 28, 2016

(87) PCT Pub. No.: WO2015/114548
PCT Pub. Date: Aug. 6, 2015

(65) Prior Publication Data
US 2016/0331848 A1    Nov. 17, 2016

(30) Foreign Application Priority Data

Jan. 29, 2014   (IT) .......................... MI2014A000121

(51) Int. Cl.
| A61K 47/20 | (2006.01) |
| A61K 9/10 | (2006.01) |
| A61B 1/31 | (2006.01) |
| A61K 49/00 | (2006.01) |
| A61K 47/34 | (2017.01) |

(52) U.S. Cl.
CPC ............. *A61K 49/006* (2013.01); *A61K 9/10* (2013.01); *A61K 47/20* (2013.01); *A61K 47/34* (2013.01)

(58) Field of Classification Search
CPC ........ A61K 49/006; A61K 47/34; A61K 9/10; A61K 47/20; A61K 9/31; A61K 9/0053; A61K 1/31

USPC ............................................................ 424/91
See application file for complete search history.

(56) References Cited

U.S. PATENT DOCUMENTS

| 2009/0175799 | A1* | 7/2009 | Tamarkin ............... A61K 8/046 424/43 |
| 2011/0052490 | A1* | 3/2011 | Vogel ................. A61B 17/3478 424/1.65 |
| 2016/0324919 | A1* | 11/2016 | Coulter .................. A61K 38/13 |

FOREIGN PATENT DOCUMENTS

| WO | 9318852 A1 | 9/1993 | |
| WO | WO-2007056439 A1 * | 5/2007 | ........... A61K 9/1617 |

OTHER PUBLICATIONS

Michael Wallace, New Strategies to Improve Polypectomy During Colonscopy, Gastroenterology & Hepatology, vol. 13, Issue 10, Supplement 3, Oct. 2017. (Year: 2017).*
Fennerty, Tissue Staining, Experimental and Investigational Endoscopy, vol. 4, Issue 2, Apr. 1994. (Year: 1994).*
Devuni, D., et al., "Chromocolonoscopy," Gastroenterol Clin N Am, 42:521-545, 2013.
Fujihira, A., et al., "The effects of internal and receptor pH on the rate of drug release from water-in-oil emulsions," Chem. Pharm. Bull. 62(1):64-71, 2014.
Miros, M., et al., "Indigocarmine chromocolonoscopy markedly increases the detection of significant polyps," Gastroenterology, 126(4)(2):A625, Apr. 2004.
International Search Report issued for PCT/IB2015/050667 dated Jun. 6, 2015, 4 pages.

* cited by examiner

*Primary Examiner* — Robert A Wax
*Assistant Examiner* — Nabila G Ebrahim
(74) *Attorney, Agent, or Firm* — Rothwell, Figg, Ernst & Manbeck, P.C.

(57) ABSTRACT

The present invention provides a novel liquid composition in the form of an emulsion or microemulsion for rectal administration comprising at least one dye, at least one emulsifier, and at least one physiologically acceptable excipient, and its use in a diagnostic endoscopic procedure of sigmoid colon and/or rectum. Preferably, said diagnostic endoscopic procedure of sigmoid colon and/or rectum is an anoscopy, a proctoscopy, a rectoscopy and/or a sigmoidoscopy.

15 Claims, No Drawings

LIQUID COMPOSITION IN THE FORM OF EMULSION OR MICROEMULSION FOR RECTAL ADMINISTRATION CONTAINING AT LEAST ONE DYE, AND ITS USE IN A DIAGNOSTIC ENDOSCOPIC PROCEDURE OF SIGMOID COLON AND/OR RECTUM

CROSS REFERENCE TO RELATED APPLICATION(S)

This application is a 35 U.S.C. § 371 National Phase Entry Application from PCT/IB2015/050667, filed 29 Jan. 2015, designating the United States, which claims priority under 35 U.S.C. § 119 to Italian application Serial No. MI2014A000121, filed 29 Jan. 2014, the entire contents of which are incorporated herein by reference.

Endoscopy is a medical examination with diagnostic purposes using a medical device called an endoscope to examine the inside of an organ or a cavity of the human body, without requiring the use of invasive surgery.

Sigmoidoscopy, a type of endoscopy, is a non-invasive medical procedure for the exploration of the last intestinal tracts, specifically the rectum and sigmoid colon (or sigma).

Sigmoidoscopy with a flexible probe allows the physician to explore the sigmoid colon (or sigma) and the rectum to diagnose the cause of disorders of various origins, such as diarrhea, inflammation, abdominal pain, or constipation. It is also used to search for polyps and possible precursors of cancer, such as, for example, adenomas. With flexible sigmoidoscopy the physician can observe intestinal bleeding due, for example, to inflammation, abnormal growths, ulcers in the sigmoid colon and rectum. Although with sigmoidoscopy it is only possible to examine a relatively small portion of intestine, the colon regions that can be explored are those with higher incidence of diseases, such as cancer of colon and rectum, and they can be a mirror of the other colon regions. The sigmoidoscope transmits an image of the interior of the rectum and sigmoid colon lumen, and in this way the physician can carefully examine the mucosa. It is also possible to perform biopsies of areas deemed suspicious, such as polyps or adenomas, by inserting into the probe the necessary instrumentation.

In many forms of endoscopy, such as colonoscopy, sigmoidoscopy and/or rectoscopy, an improvement in conventional diagnostic techniques has recently been achieved by resorting to the use of pharmaceutical formulations containing dyes (such as, for example, methylene blue, Congo red, indigo carmine and toluidine blue), useful for their ability to produce in situ a staining able to amplify the details of the mucosa structure, highlighting, through differential absorptions, abnormalities and/or possible pathologies associated with them. The endoscopy performed using preparations containing dyes is called chromoendoscopy.

The chromoendoscopy is based on the principle that the tissues or mucosa affected by pathological phenomena, inflammatory processes or lesions of various origins are stained differently than healthy tissues or mucosa. Tissue staining is useful to characterize and classify the type of identified pathology, to detect lesions of the mucosa and to delineate the edges. The precise delineation of the edges of a lesion is particularly important when there is then the need to proceed to its resection or ablation. In colonoscopy, sigmoidoscopy and rectoscopy, the chromoendoscopy is used with the main purpose to detect, characterize and delineate the edges of polyps, pseudo-polyps, adenomas, pre-neoplastic lesions and neoplasms. In the case of diminutive and flat polyps, particularly difficult to detect with common endoscopic techniques, chromoendoscopy leads to an increase of detection capability: the endoscopist is able to identify topographical features that have a high degree of correlation with their histology. The technique of endoscopic magnification (thanks to which it is possible to obtain a magnification of the mucosa surface almost to the microscopic level) in association with chromoendoscopy allowed endoscopists to study and classify the lesions of the colon mucosa, such as polyps, adenomas and neoplasms, according to their "pit pattern", namely based on the appearance of the dimples that constitute the mucosa surface. The possibility to accurately predict the histology of polyps and adenomas based on the endoscopic examination alone, thanks to the use of techniques such as chromoendoscopy and magnification endoscopy, has the great advantage of lowering the costs for colon cancer screening, reducing the need for the lesions well characterized by these techniques, to perform biopsies, which are limited only to lesions of difficult classification and characterization. Another use of chromoendoscopy is the evaluation and characterization of the colonic mucosa in chronic inflammatory diseases such as ulcerative colitis.

Currently, the most commonly adopted practice in chromoendoscopy provides for the spray application of a small amount of dye solution on the mucosa, by means of a catheter placed within the endoscope probe. After 1 or 2 minutes of application, rinsing and aspiration of dye in excess is usually performed. The dye diffusion and its possible absorption by the cells of the mucosa markedly differentiate normal cells from abnormal ones, such as those in advanced stage of replication, a characteristic of cancer.

The dyes used in chromoendoscopy are classified as follows: vital (or "absorptive"), contrast and reactive ones. The vital dyes, such as toluidine blue and methylene blue, identify specific epithelial cells types by preferential adsorption or diffusion across the cell membrane; the non-vital dyes (or contrast) as indigo carmine, seep through mucosal crevices and highlight surface topography and mucosal irregularities; reactive dyes, such as Congo red and phenol red, undergo chemical reactions with specific cellular constituents, resulting in a change in color similar to a pH indicator However, the standard chromoendoscopy techniques pose important issues to clinical institutions: the pharmacy of the institution where the endoscopies are performed must be able to prepare, stabilize and sterilize the dyes aqueous solutions, generally having a concentration of between 0.1% and 1%; the endoscope must be provided with a channel for the insertion of the catheter necessary for the application of the staining solution; the dye should be distributed evenly over the surface of the mucosa. In addition, the aqueous solutions do not adhere to the mucosa walls, and can therefore flow from the cavity, especially in the case of anoscopy, proctoscopy, sigmoidoscopy and/or rectoscopy (for example from the rectum). In addition, the rinsing may wash the walls of the mucosa too early, not leaving the dye enough time to adequately stain the surface; this is especially true when vital dyes (such as methylene blue or toluidine blue), which must be absorbed by the mucosa to exert their properties, are used. The above mentioned reasons contribute to make it difficult to perform chromoendoscopy procedures that currently can only be performed in the best diagnostic centers, and with a significant time and resources investment. It should also be emphasized that recourse to the use of the dye by spraying a solution, as expected in the standard chromoendoscopy procedures, is chosen by the endoscopist only in case of doubt about the normality of the intestinal area under observation; it is therefore inherent in such procedures a discretionary parameter that depends on each endoscopist specific sensitivity and experience, notoriously diverse at the individual level.

There is therefore the need to provide a new composition, especially for use in diagnostic endoscopic of sigmoid colon and/or rectum, and in particular in anoscopy, proctoscopy, rectoscopy and/or sigmoidoscopy, that allows the administration of the dye in a simpler and safer way, that removes the criterion of the analyst subjectivity, and at the same time guarantees a better staining efficacy, resulting in better identification of the pathological and/or non-pathological areas. It has now surprisingly been found that a liquid composition in the form of an emulsion or microemulsion for rectal administration, comprising at least one dye, at least one emulsifier, and at least one physiologically acceptable excipient is capable of allowing the dye to reach the desired area and remain there longer, obtaining the improved contrast required during the endoscopic diagnostic examination of sigmoid colon and/or rectum, preferably in case of anoscopy, proctoscopy, sigmoidoscopy and/or rectoscopy.

It was also surprisingly found that such a liquid composition in the form of an emulsion or microemulsion ensures effective cleansing of the desired area, contributing to the improved visualization of the same during the diagnostic endoscopic procedure.

DESCRIPTION

The present invention provides a liquid composition in the form of an emulsion or microemulsion for rectal administration comprising at least one dye, at least one emulsifier, and at least one physiologically acceptable excipient, and its use in a diagnostic endoscopic procedure of sigmoid colon and/or rectum. Preferably, said diagnostic endoscopic procedure of sigmoid colon (also called sigma) and/or of rectum is an anoscopy, a proctoscopy, a rectoscopy and/or a sigmoidoscopy.

It was surprisingly found that, by incorporating at least one dye in a liquid composition in the form of an emulsion or microemulsion, containing at least one emulsifier according to the invention described herein, instead of preparing a simple solution of the dye (such as an aqueous solution), it is possible to obtain a formulation with improved characteristics, such as to optimize the staining of the mucosa of the inner cavities of the body organs, preferably the mucosa of the rectum and/or sigmoid colon (also called sigma).

Specifically, by incorporating at least one dye in a liquid composition in the form of an emulsion or microemulsion, containing at least one emulsifier, according to the invention described herein, the following advantages were surprisingly found: from a pharmaceutical-technological point of view, said at least one emulsifier plays a role of primary importance in stabilizing the emulsion or the microemulsion as, by positioning at the interphase between the dispersed phase and the dispersing phase, it confers stability to the dispersed system and prevents destabilization phenomena such as creaming, coalescence, flocculation or sedimentation, which commonly involve the breaking of the emulsion or microemulsion. From a physiological point of view, said at least one emulsifier acts as permeation promoter, promoting the absorption of the dye through the mucosa, preferably of the sigmoid colon (sigmoid) and/or rectum. Said at least one emulsifier may also act as a detergent or cleansing agent favoring the dissolution and/or dispersion and/or removal of fecal material, feces and/or mucus (cleansing), ensuring an efficient cleansing of the desired area during the step in preparation of the diagnostic endoscopic investigation, thus contributing to the improved visualization of said area during the diagnostic endoscopic procedure. According to the invention described herein, further physiologically acceptable excipients may contribute, through different mechanisms, to increase the dye absorption by the mucosa of sigmoid colon and/or rectum. These excipients may also exert a dual role: a pharmaceutical-technological role, contributing to the stabilization of the emulsion or microemulsion; and a physiological role, helping to increase the dye absorption by the mucosa of sigmoid colon and/or rectum, and/or promoting the removal of fecal material, feces and/or mucus.

Specifically, said at least one physiologically acceptable excipient useful in the composition object of the present invention may preferably be selected from:

1) Lipophilic compounds: from a pharmaceutical-technological point of view, the lipophilic compounds constitute the oily phase (also simply called "oil") of the emulsion or microemulsion according to the invention described herein. From a physiological point of view, many lipophilic compounds are able to act as permeation promoting agents, promoting the absorption of the dye through the mucosa, preferably of sigmoid colon and/or rectum. The lipophilic compounds are also able to act as lubricants by favoring the expulsion of the fecal material, feces and/or mucus (cleansing).

2) Co-emulsifiers: from a pharmaceutical-technological point of view, the co-emulsifiers can be used as optional components of the emulsion or microemulsion according to the invention described herein, as they contribute, together with the emulsifiers, to its stabilization. From a physiological point of view, many co-emulsifiers are able to act as permeation promoting agents, promoting the absorption of the dye through the mucosa, preferably of sigmoid colon and/or rectum.

3) Viscosity modifying agents: from a pharmaceutical-technological point of view, viscosity modifying agents contribute to stabilization of the emulsion or microemulsion according to the invention described herein, since, by increasing the viscosity of the formulation, they make the phenomenon of the coalescence of the dispersed phase droplets more difficult; from a physiological point of view, many viscosity modifying agents possess bio-adhesive properties, and contribute to adhere the composition of the present invention to the walls of the mucosa, preferably of the sigmoid colon and/or rectum, thus increasing the contact time between the emulsion or microemulsion and the mucosal wall, determining, in the case of a vital dye, a greater probability of absorption.

4) Inverse thermosensitive polymers: from a pharmaceutical-technological point of view, the inverse thermosensitive polymers contribute to the stabilization of the emulsion or microemulsion according to the invention described herein, since, by increasing the viscosity of the formulation, they make the phenomenon of coalescence of the dispersed phase droplets more difficult; from a physiological point of view, the inverse thermosensitive polymers contribute to enhance the adhesion of the emulsion or microemulsion according to the invention described herein, to the mucosa walls, preferably of the sigmoid colon and/or rectum, as the addition of said polymer emulsion or microemulsion of the invention, at a concentration greater than the critical gelation concentration (CGC), guarantees an increase of the viscosity of said emulsion or microemulsion, in response to an increase in temperature, preferably from room temperature (i.e. about 20-25° C.) to body temperature (i.e. about 37° C.).

This helps to increase the contact time between said emulsion or microemulsion and the walls of the mucosa. The inverse thermosensitive polymers may also act as surfactants, lowering the surface tension in situ, thereby contributing to removal of fecal material, feces and/or mucus.

It was also surprisingly discovered that the use of physiologically acceptable excipients belonging to the classes listed above may confer peculiar properties to the emulsion or microemulsion containing at least one dye according to the present invention. Any mixture of the physiologically acceptable excipients mentioned above may be used according the present invention.

It was found that, thanks to the liquid formulation in the form of an emulsion or microemulsion according to the invention described herein, it is possible to obtain a composition containing at least one dye capable of optimizing the staining of the mucosa of the internal cavities and organs of the body, preferably of the mucosa of the rectum and/or sigmoid colon, through at least one of the following mechanisms:

1) increase the absorption of the dye due to the ability, characteristic of the emulsion or microemulsion according to the present invention, to facilitate the passage of the dye itself through the cell membrane of the epithelial cells of the mucosa of the sigmoid colon and/or rectum. This staining is mainly on the surface layer of the sigmoid colon and/or rectum (pigmentation) mucosa; and/or 2) increase the contact time between the emulsion or microemulsion according to the present invention and the walls of the mucosa of the sigmoid colon and/or rectum. Furthermore, the possible use of viscosity modifying agents with bio-adhesive properties and/or inverse thermosensitive polymers may increase the adhesion to the mucosa walls of the emulsion or microemulsion according to the present invention (muco-adhesive properties), with formation of a film having a reduced tendency to flow along the walls themselves, compared to the solutions known in the state of the art (for example, simple aqueous solutions). As a result, the dye dissolved in the peculiar liquid composition, in the form of an emulsion or microemulsion object of the present invention, remains in contact with the cell membrane of the epithelial cells of the mucosa for a longer period of time, as compared to the dye dissolved in a composition formulated in the form of a solution (for example, a simple aqueous solution). It was surprisingly discovered that the combination of these characteristics confer certain advantages to the liquid composition in the form of an emulsion or microemulsion according to the invention described herein, compared to the compositions known up to now in the state of the art, such as solutions of dyes commonly used in this technical field (for example, aqueous solutions).

These features are particularly advantageous when the liquid composition in the form of an emulsion or microemulsion object of the present invention contains a vital dye (or "absorptive"), such as methylene blue, toluidine blue, fluorescein or Lugol's solution. In fact, by their nature, said vital dyes must be absorbed by the cells in order to exert their staining properties. The longer a vital dye remains in contact with the cell membrane, the greater is the amount of dye that can be absorbed by the epithelial cells, and the greater is the staining effect obtained and the contrast viewable during the endoscopic diagnosis.

Thanks to the characteristics listed above, it is thus possible to advantageously maximize the staining effect, also using reduced amounts of dye. It is a great advantage to be able to include the above mentioned dyes in a formulation able to promote, by means of one or more of the above described mechanisms, their permeation through the cell membranes of epithelial cells of the mucosa, as well as to promote and increase their adhesion to the wall of the membranes themselves, preferably of the sigmoid colon and/or rectum.

The time available to obtain the absorption of the dye is, usually, equal to a few minutes, and it is therefore felt the need to obtain a penetration within the walls of the mucosa to increase the contrast between the intracellular space and cell membranes, in such a way to maximize the staining and its retention time.

The emulsion or microemulsion object of the present invention allows to obtain a more even, more visible and more durable staining compared to that obtainable by means of the simple dye solutions hitherto known in the state of the art (for example, aqueous solutions).

The increased absorption of the dye by the mucosal epithelial cells, preferably of the sigmoid colon and/or rectum, determines a significant improvement in the visualization of the areas of diagnostic interest (preferably the sigmoid colon and/or rectum).

In fact, as described above, the tissues and mucosae affected by pathological conditions or lesions of various natures are stained differently than the healthy mucosae or tissues. Obtainment of a different staining between healthy tissue and tissue with pathological phenomena is important in order to amplify the contrast with the pathological areas.

By way of example, dysplasia, polyps, lesions and cancers of the sigmoid colon and/or rectum may be the better and earlier visualized, the more evident, during the endoscopic diagnostic examination, is the difference in coloration between the pathological tissue and surrounding normal mucosa.

It is also a great advantage to be able to ensure effective cleansing of the desired area, thus contributing to its improved visualization during the diagnostic endoscopic procedure. In order to achieve the best chance of observation, an optimal degree of cleanliness is indeed important.

As mentioned above, thanks to its peculiar formulation, the liquid composition in the form of an emulsion or microemulsion of the invention ensures an optimal degree of cleanliness. Specifically, the presence in the composition of at least one emulsifier promotes the dissolution and/or dispersion and/or removal of fecal material, feces and/or mucus that may be present in the area of investigation.

In addition, the possible presence of at least one lipophilic compound and/or the possible presence of at least one inverse thermosensitive polymer can contribute to the dissolution and/or dispersion and/or removal of fecal material, feces and/or mucus.

The effective cleansing and the optimal staining advantageously lead to an improved visualization of the mucosa, especially of the sigmoid colon and/or rectum during the diagnostic endoscopic procedure.

The tissues and mucosae affected by pathological conditions or lesions of various natures can thus be better observed, thus improving the possibility of identification of the pathological areas.

For example, dysplasias, polyps, tightened lesions and cancers of the sigmoid colon and/or rectum can be much better and much earlier visualized as much cleaner the affected area is during the diagnostic endoscopic procedure.

The invention described herein thus provides a liquid composition in the form of an emulsion or microemulsion for rectal administration comprises at least one dye, at least one emulsifier, and at least one physiologically acceptable excipient, and its use in a diagnostic endoscopic procedure of rectum and/or the sigmoid colon. Preferably, said diagnostic endoscopic procedure of rectum and/or sigmoid colon is an anoscopy, a proctoscopy, a rectoscopy and/or a sigmoidoscopy. Preferably, said diagnostic endoscopic procedure comprises the administration of the liquid composition in the form of an emulsion or microemulsion according to the invention to humans. Preferably, the composition of the invention is administered during the preparation phase of the diagnostic endoscopic investigation.

The invention described herein also provides a method for performing a diagnostic endoscopic procedure of sigmoid colon and/or rectum, said method comprising the rectal administration of a liquid composition in the form of an emulsion or microemulsion, wherein said composition in the form of an emulsion or microemulsion comprises at least one dye, at least one emulsifier, and at least one physiologically acceptable excipient. Preferably, said diagnostic endoscopic procedure of rectum and/or sigmoid colon is an anoscopy, a proctoscopy, a rectoscopy and/or a sigmoidoscopy. Preferably, said method comprises the administration of said composition during the preparation phase of the diagnostic endoscopic investigation. Preferably, said method includes the administration of a liquid composition in the form of an emulsion or microemulsion according to the invention to humans.

According to the present invention, the liquid composition in the form of an emulsion or microemulsion may preferably be a "water in oil", "oil in water", "oil in water in oil" and/or "water in oil in water" emulsion or microemulsion. In a preferred embodiment, the composition in the form of an emulsion or microemulsion is an "oil in water" emulsion.

According to one embodiment, the liquid composition in the form of an emulsion or microemulsion for rectal administration comprises:
a) an aqueous phase;
b) an oily phase;
c) at least one dye;
d) at least one emulsifier;
e) at least one physiologically acceptable excipient.

Preferably, said composition is for use in a diagnostic endoscopic procedure of sigmoid colon and/or rectum; said diagnostic endoscopic procedure of the sigmoid colon and/or rectum is then more preferably an anoscopy, a proctoscopy, a rectoscopy and/or a sigmoidoscopy.

According to one embodiment, the liquid composition in the form of an emulsion or microemulsion for rectal administration consists essentially of:
a) an aqueous phase;
h) an oily phase;
c) at least one dye;
d) at least one emulsifier;
e) at least one physiologically acceptable excipient.

Preferably, said composition is for use in a diagnostic endoscopic procedure of sigmoid colon and/or rectum; said diagnostic endoscopic procedure of the sigmoid colon and/or rectum is then more preferably an anoscopy, a proctoscopy, a rectoscopy and/or a sigmoidoscopy.

According to one embodiment, the liquid composition in the form of an emulsion or microemulsion for rectal administration comprises:
a) an aqueous phase;
b) an oily phase;
c) at least one dye;
d) at least one emulsifier;
e) optionally at least one co-emulsifier
f) at least one physiologically acceptable excipient.

Preferably, said composition is for use in a diagnostic endoscopic procedure of sigmoid colon and/or rectum; said diagnostic endoscopic procedure of the sigmoid colon and/or rectum is then more preferably an anoscopy, a proctoscopy, a rectoscopy and/or a sigmoidoscopy.

According to one embodiment, the liquid composition in the form of an emulsion or microemulsion for rectal administration consists essentially of:
a) an aqueous phase;
b) an oily phase;
c) at least one dye;
d) at least one emulsifier;
e) optionally at least one co-emulsifier
f) at least one physiologically acceptable excipient.

Preferably, said composition is for use in a diagnostic endoscopic procedure of sigmoid colon and/or rectum; said diagnostic endoscopic procedure of the sigmoid colon and/or rectum is then more preferably an anoscopy, a proctoscopy, a rectoscopy and/or a sigmoidoscopy.

According to one embodiment, the liquid composition in the form of an emulsion or microemulsion for rectal administration comprises:
a) an aqueous phase;
b) an oily phase;
c) at least one dye;
d) at least one emulsifier;
e) optionally at least one co-emulsifier optionally at least one viscosity modifying agent;
g) at least one physiologically acceptable excipient.

Preferably, said composition is for use in a diagnostic endoscopic procedure of sigmoid colon and/or rectum; said diagnostic endoscopic procedure of the sigmoid colon and/or rectum is then more preferably an anoscopy, a proctoscopy, a rectoscopy and/or a sigmoidoscopy.

According to one embodiment, the liquid composition in the form of an emulsion or microemulsion for rectal administration consists essentially of:
a) an aqueous phase;
b) an oily phase;
c) at least one dye;
d) at least one emulsifier;
e) optionally at least one co-emulsifier optionally at least one viscosity modifying agent;
g) at least one physiologically acceptable excipient.

Preferably, said composition is for use in a diagnostic endoscopic procedure of sigmoid colon and/or rectum; said diagnostic endoscopic procedure of the sigmoid colon and/or rectum is then more preferably an anoscopy, a proctoscopy, a rectoscopy and/or a sigmoidoscopy.

According to one embodiment, the liquid composition in the form of an emulsion or microemulsion for rectal administration comprises:
a) an aqueous phase;
b) an oily phase;
c) at least one dye;
d) at least one emulsifier;
e) optionally at least one co-emulsifier
f) optionally at least one inverse thermosensitive polymer;
g) at least one physiologically acceptable excipient.

Preferably, said composition is for use in a diagnostic endoscopic procedure of sigmoid colon and/or rectum; said diagnostic endoscopic procedure of the sigmoid colon and/or rectum is then more preferably an anoscopy, a proctoscopy, a rectoscopy and/or a sigmoidoscopy.

According to one embodiment, the liquid composition in the form of an emulsion or microemulsion for rectal administration consists essentially of:

a) an aqueous phase;
b) an oily phase;
c) at least one dye;
d) at least one emulsifier;
e) optionally at least one co-emulsifier
f) optionally at least one inverse thermosensitive polymer;
g) at least one physiologically acceptable excipient.

Preferably, said composition is for use in a diagnostic endoscopic procedure of sigmoid colon and/or rectum; said diagnostic endoscopic procedure of the sigmoid colon and/or rectum is then more preferably an anoscopy, a proctoscopy, a rectoscopy and/or a sigmoidoscopy.

According to one embodiment, the liquid composition in the form of an emulsion or microemulsion for rectal administration comprises:
a) an aqueous phase;
b) an oily phase;
c) at least one dye;
d) at least one emulsifier;
e) optionally at least one co-emulsifier
f) optionally at least one viscosity modifying agent;
g) optionally at least one inverse thermosensitive polymer;
h) at least one physiologically acceptable excipient.

Preferably, said composition is for use in a diagnostic endoscopic procedure of sigmoid colon and/or rectum; said diagnostic endoscopic procedure of the sigmoid colon and/or rectum is then more preferably an anoscopy, a proctoscopy, a rectoscopy and/or a sigmoidoscopy.

According to one embodiment, the liquid composition in the form of an emulsion or microemulsion for rectal administration consists essentially of:
a) an aqueous phase;
b) an oily phase;
c) at least one dye;
d) at least one emulsifier;
e) optionally at least one co-emulsifier
f) optionally at least one viscosity modifying agent;
g) optionally at least one inverse thermosensitive polymer;
h) at least one physiologically acceptable excipient.

Preferably, said composition is for use in a diagnostic endoscopic procedure of sigmoid colon and/or rectum; said diagnostic endoscopic procedure of the sigmoid colon and/or rectum is then more preferably an anoscopy, a proctoscopy, a rectoscopy and/or a sigmoidoscopy.

By the term "aqueous phase" it is meant one of the phases of the emulsion or microemulsion, which may constitute the dispersing phase or the dispersed phase of the emulsion, and which is constituted by an aqueous solution comprising water-soluble components of the emulsion in dissolved form. By the term "organic phase" or "oil phase" or "oily phase" it is meant one of the phases of the emulsion or microemulsion, comprising at least one lipophilic compound.

In the preparation of the liquid composition in the form of an emulsion or microemulsion according to the invention described herein, said at least one dye may be selected from vital dyes (or absorptive), non-vital dyes (or contrast) and/or reactive dyes. The vital dyes (or absorptive), such as Lugol's solution, fluorescein, and methylene blue identify specific types of epithelial cells by preferential absorption or diffusion through the cell membrane; non-vital dyes (or contrast), as indigo carmine, seep through the crevices of the mucous membranes and highlight the surface topography and mucosal irregularities; reactive dyes, such as Congo red and phenol red, undergo chemical reactions with specific cellular constituents, thus resulting in a change in color similar to a pH indicator. According to the invention described herein, said vital dye (or absorptive) may be chosen from the group comprising, but not limited to: Lugol's solution, methylene blue, toluidine blue, cresyl violet, fluorescein and/or the like, and/or salts thereof. According to the invention described herein, said non-vital dye (or contrast) may be chosen from the group comprising, but not limited to: indigo carmine and/or the like.

According to the invention described herein, said reactive dye may be chosen from the group comprising, but not limited to: Congo red, phenol red and/or the like. Any mixture of the dyes mentioned above can be used to form the appropriate composition. According to a preferred embodiment, said at least one dye is methylene blue. According to another preferred embodiment, said at least one dye is indigo carmine. According to another preferred embodiment, said at least one dye is fluorescein or a salt thereof (sodium fluorescein).

According to the invention described herein, said at least one dye is contained in an amount ranging from about 0.0005 g/100 ml to about 2.0 g/100 ml (from about 0.0005% w/v to about 2.0% w/v), preferably from about 0.001 g/100 ml to about 1.0 g/100 ml (from about 0.001% w/v to about 1.0% w/v), more preferably from about 0.002 g/100 ml to about 0.5 g/100 ml (from about 0.002% w/v to about 0.5% w/v). According to an embodiment, said at least one dye is contained in the composition in an amount of about 0.002 g/100 ml (about 0.002% w/v).

According to another embodiment, said at least one dye is contained in the composition in an amount of about 0.004 g/100 ml (about 0.004% w/v).

According to a further embodiment, said at least one dye is contained in the composition in an amount of about 0.006 g/100 ml (about 0.006% w/v).

According to a further embodiment, said at least one dye is contained in the composition in an amount of about 0.008 g/100 ml (about 0.008% w/v).

According to a further embodiment, said at least one dye is contained in the composition in an amount of about 0.01 g/100 ml (about 0.01% w/v). According to a further embodiment, said at least one dye is contained in the composition in an amount of about 0.02 g/100 ml (about 0.02% w/v). According to a further embodiment, said at least one dye is contained in the composition in an amount of about 0.04 g/100 nil (about 0.04% w/v). According to a further embodiment, said at least one dye is contained in the composition in an amount of about 0.05 g/100 ml (about 0.05% w/v). According to a further embodiment, said at least one dye is contained in the composition in an amount of about 0.1 g/100 ml (about 0.1% w/v). According to a further embodiment, said at least one dye is contained in the composition in an amount of about 0.2 g/100 ml (about 0.2% w/v). According to a further embodiment, said at least one dye is contained in the composition in an amount of about 0.5 g/100 ml (about 0.5% w/v).

According to a preferred embodiment, said at least one dye is contained in the composition of the invention in an amount of about 0.01 g/100 ml (about 0.01% w/v) or of about 0.02 g/100 ml (about 0.02% w/v).

The above quantities are expressed in grams per 100 ml of the liquid composition in the form of an emulsion or microemulsion of the invention, or in percentage weight/volume of the composition.

In the preparation of the liquid composition in the form of an emulsion or microemulsion according to the invention described herein, said at least one emulsifier may be selected from non-ionic emulsifiers, ionic emulsifiers, natural emulsifiers, or mixtures thereof.

The presence of said at least one emulsifier in the liquid composition of the invention significantly improves the characteristics of the composition itself. Said at least one emulsifier was surprisingly been found to act as a promoter of the permeation in the absorption and/or diffusion of the dye through the cell membrane of the mucosa epithelial cells, thus allowing the dye to improve the lesions visibility.

Said at least one emulsifier may also act as a detergent or cleansing agent favoring the dissolution and/or dispersion and/or removal of fecal material, feces and/or mucus (cleansing) in the area of investigation.

The use of at least one emulsifier in the composition according to the invention described herein brings a great advantage over the common formulation of a dye in the form of a simple solution (e.g. aqueous solution).

In other words, the presence of said at least one emulsifier in the liquid composition in the form of an emulsion or microemulsion according to the invention has a dual role: first of all, it performs a pharmaceutical-technological function as, positioning itself at the interphase between the dispersed phase and the dispersing phase, it prevents the coalescence of the dispersing phase drops, thus stabilizing the emulsion; secondly, it exerts a surprising physiological function, acting as a promoter of the permeation in the absorption or diffusion of the dye through the cell membranes of the mucosa epithelial cells, after rectal administration of the composition. As mentioned above, the staining mainly takes place on the surface layer of the mucosa (pigmentation).

The above-mentioned ability of the emulsifier to act physiologically on the absorption and/or diffusion of the dye through the cells of the mucosa is particularly advantageous when the composition of the present invention contains a vital dye (or "absorptive"), such as the methylene blue, toluidine blue, Lugol's solution or a mixture thereof.

According to the invention described herein, said at least one emulsifier may be a non-ionic emulsifier, preferably selected from the group comprising, but not limited to: monoesters of fatty acids with polyethylene glycol such as PEG-30 stearate, PEG-40 laurate, PEG-40 oleate, PEG-40 stearate, PEG-100 stearate and/or the like; diesters of fatty acids with polyethylene glycol such as PEG-4 dilaurate, PEG-32 dioleate, PEG-400 dioleate and/or the like; esters of fatty acids with polyglycerin, such as polyglyceryl-6 dioleate, polyglyceryl-6 distearate, polyglyceryl-3 monooleate and/or the like; esters of fatty acids with polyethylene glycol-sorbitan, such as PEG-20 sorbitan monolaurate, PEG-20 sorbitan monopalmitate, PEG-20 sorbitan monostearate and/or the like; alkyl ethers with polyethylene glycol, such as PEG-2 oleyl ether, PEG-3 oleyl ether, PEG-5 oleyl ether, PEG-20 oleyl ether, PEG-4 lauryl ether, PEG-32 lauryl ether, PEG-20 cetostearyl ether, cetomacrogol 1000 and/or the like; esters of fatty acids with sucrose, such as sucrose distearate; esters of fatty acids with sorbitan, come sorbitan monolaurate, sorbitan monopalmitate, sorbitan monooleate, sorbitan monostearate and/or the like; esters of fatty acids with polyoxyethylene-sorbitan, such as polysorbate 20, polysorbate 60, polysorbate 80 and/or the like; poloxamers, such as, for example, poloxamer 124, poloxamer 188, poloxamer 237, poloxamer 338, poloxamer 407 and/or the same; esters of fatty acids with propylene glycol; derivatives of castor oil with polyoxyethylene, such as polyoxyl-5 castor oil, polyoxyl-15 castor oil, polyoxyl-35 castor oil, polyoxyl-40 hydrogenated castor oil and/or the like; caprylocaproyl macrogol-8 glycerides (commercially known under the trade name Labrasol®); esters of stearic acid with polyoxyethylene (also called esters of stearic acid with polyethylene glycol), such as polyoxyethylene (20) stearate, polyoxyethylene (40) stearate, polyoxyethylene (100) stearate, polyoxyl-15-hydroxystearate (Solutor HS15); polyoxyethylene alkyl ethers, such as polyoxyethylene cetyl ether, polyoxyethylene palmityl ether, polyoxyethylene exadecyl ether; fatty alcohol ethoxylates, commercially known under the trade name Brij®, such as Brij® L23, Brij® C20, Brij® S2, Brij® S20; a monoglyceride; a diglyceride; isoceteth-20; steareth-2; glyceryl monostearate/ PEG 100 stearate; steareth-21; laureth 4; ceteareth 16; ceteareth 20; steareth 10; steareth 20; ceteth 20; macrogol cetostearyl ether; ceteth 2; cetomacrogol ether; steareth-2.

Any mixture of non-ionic emulsifiers mentioned above may be used to form the appropriate composition. According to a preferred embodiment, said at least one emulsifier is PEG-40 stearate (polyethylene glycol-40 stearate). According to a preferred embodiment, said at least one emulsifier is PEG-20 sorbitan monolaurate (polyethylene glycol 20 sorbitan monolaurate, commercially also known as Tween® 20). According to a preferred embodiment, said at least one emulsifier is poloxamer 407 (known under the trade name Kolliphor® P407). According to another preferred embodiment, said at least one emulsifier is caprylocaproyl macrogol-8 glycerides (known under the trade name Labrasol®). According to another preferred embodiment, said at least one emulsifier is polysorbate 80 (known under the trade name Tween® 80). According to another preferred embodiment, said at least one emulsifier is propylene glycol monocaprylate (known under the trade name Capryol® 90). According to another preferred embodiment, said at least one emulsifier is lauroyl macrogol-32 glycerides (known under the trade name Gelucire® 44/14). More preferably, said at least one emulsifier is caprylocaproyl macrogol-8 glycerides (Labrasol®), polyoxyl-15-hydroxystearate (Solutol® HS15), poloxamer 407 and/or a mixture thereof.

According to the invention described herein, said at least one emulsifier may be an ionic emulsifier and may be selected from the group comprising, but not limited to: anionic surfactants such as alkyl sulfate salts, such as sodium dodecyl sulfate, sodium lauryl sulfate, alkyl benzene sulfonate and the like; fatty acids salts or mixtures thereof; cationic surfactants such as cetyl trimethylammonium bromide, cetylpyridinium chloride, benzalkonium chloride and/ or the like; zwitterionic surfactants such as dodecyl betaine, cocamidopropyl betaine and cocoamphoglycinate and/or the like. Any mixture of the above ionic emulsifiers may be used to form the appropriate composition. According to an embodiment, said at least one emulsifier is sodium lauryl sulfate.

According to the invention described herein, said at least one emulsifier may be a natural emulsifier and may be selected from the group comprising, but not limited to: egg lecithin, hydrogenated phosphatidylcholine, unsaturated phosphatidylcholine, soya lecithin, hydrogenated soy lecithin, glycerophosphocholine, soybean lysolecithin, phospholipids, hydrogenated phospholipids and/or the like. Any mixture of natural emulsifiers mentioned above may be used to form the appropriate composition. According to an embodiment, said at least one emulsifier is egg lecithin. According to another embodiment, said at least one emulsifier is soya lecithin. According to another embodiment, said at least one emulsifier is hydrogenated phosphatidylcholine.

Any mixture of the emulsifiers mentioned above may be used to form the appropriate composition. According to the invention described herein, said at least one emulsifier is contained in an amount ranging from about 0.1 g/100 ml to about 50.0 g/100 ml (from about 0.1% w/v to about 50.0% w/v), preferably from about 0.2 g/100 ml to about 30.0 g/100 ml (from about 0.2% w/v to about 30.0% w/v), more preferably from about 0.5 g/100 ml to about 25.0 g/100 ml (from about 0.5% w/v to about 25.0% w/v), much more preferably from about 1.0 g/100 ml to about 10.0 g/100 ml (from about 1.0% w/v to about 10.0% w/v). According to an embodiment, said at least one emulsifier is contained in an amount of about 1.0 g/100 ml (about 1.0% w/v). According to an embodiment, said at least one emulsifier is contained in an amount of about 1.5 g/100 ml (about 1.5% w/v). According to an embodiment, said at least one emulsifier is contained in an amount of about 2.0 g/100 ml (about 2.0% w/v). According to another embodiment, said at least one emulsifier is contained in an amount of about 2.5 g/100 ml (about 2.5% w/v). According to another embodiment, said at least one emulsifier is contained in an amount of about 5.0 g/100 ml (about 5.0% w/v). According to another embodiment, said at least one emulsifier is contained in an amount of about 8.0 g/100 ml (about 8.0% w/v). According to another embodiment, said at least one emulsifier is contained in an amount of about 10.0 g/100 ml (about 10.0 w/v).

The above quantities are expressed in grams per 100 ml of the liquid composition in the form of an emulsion or microemulsion, or in percentage weight/volume of the composition.

According to the invention described herein, the said composition in the form of emulsion or microemulsion may contain at least one co-emulsifier. Said at least one co-emulsifier plays a dual role in the emulsion or microemulsion object of the present invention: first of all it exerts a pharmaceutical-technological function as, together with the emulsifiers, it helps stabilize the emulsion, preventing phenomena such as creaming, flocculation, sedimentation or coalescence; and secondly, it exerts a physiological function, acting as a promoter of the permeation in the absorption or the diffusion of the dye through the cell membranes of the mucosa epithelial cells, after rectal administration of the composition. In the preparation of compositions in the form of emulsions or microemulsions according to the invention described herein, said at least one co-emulsifier may be selected in the groups comprising, but not limited to: short and medium chain alcohols, such as ethanol, propanol, isopropanol and/or the like; glycols, such as propylene glycol and the like; diethylene glycol monoethyl ether (known under the trade name Transcutol®); polyethylene glycols, such as PEG 200, PEG 300, PEG 400 and/or the like; DMSO (dimethyl sulfoxide); long chain alcohols, such as cetyl alcohol, myristic alcohol, oleic alcohol and/or the like; glycerol; short-chain esters, such as ethyl acetate, ethyl lactate and/or the like; fatty acid esters, such as ethyl oleate, isopropyl myristate, isopropyl palmitate and/or the like; fatty acids, such as oleic acid, myristic acid and/or the like; fatty acid salts, such as sodium oleate, sodium palmitate, sodium stearate and/or the like. Any mixture of the co-emulsifiers mentioned above may be used to form the appropriate composition. In one embodiment, the co-emulsifier is propylene glycol. In another embodiment, the co-emulsifier is glycerol. In another embodiment, the co-emulsifier is sodium oleate. In a preferred embodiment, the co-emulsifier is diethylene glycol monoethyl ether (known under the trade name Transcutol®).

According to the present invention, said at least one co-emulsifier is contained in an amount ranging from 0.001 g/100 ml to about 50.0 g/100 ml (from about 0.001% w/v to about 50.0% w/v), preferably from about 0.01 g/100 ml to about 20.0 g/100 ml (from about 0.01% w/v to about 20.0% w/v), more preferably from about 0.02 g/100 ml to about 10.0 g/100 ml (from about 0.02% w/v to about 10.0% w/v). According to an embodiment, said at least one co-emulsifier is contained in an amount of about 0.02 g/100 ml (about 0.02% w/v). According to an embodiment, said at least one co-emulsifier is contained in an amount of about 1.0 g/100 ml (about 1.0% w/v). According to another embodiment, said at least one co-emulsifier is contained in an amount of about 2.5 g/100 ml (about 2.5% w/v). According to another embodiment, said at least one co-emulsifier is contained in an amount of about 5.0 g/100 ml (about 5.0% w/v). According to another embodiment, said at least one co-emulsifier is contained in an amount of about 7.0 g/100 ml (about 7.0% w/v). According to another embodiment, said at least one co-emulsifier is contained in an amount of about 10.0 g/100 ml (about 10.0% w/v).

According to the invention described herein, the composition in the form of an emulsion or microemulsion may comprise at least one viscosity modifying agent. Said viscosity modifying agent is useful for stabilizing the emulsion or microemulsion, and to control the permanence of the dye in the target organs. Said viscosity modifying agent thus plays an important physiological role by enhancing the adhesiveness of the composition object of the invention to the mucosa walls, increasing the time of contact between the emulsion or microemulsion and the mucosa itself.

According to the invention described herein, said at least one viscosity modifying agent may be a natural compound, selected from the group comprising, but not limited to: sodium alginate, sodium caseinate, egg albumin, agar gelatin, carrageenan, natural rubber such as xanthan gum, gum tragacanth, guar gum, hydroxypropyl guar gum, starch, amino groups-containing polymers such as, for example, chitosan, acidic polymers obtainable from natural sources such as, for example, alginic acid, hyaluronic acid and salts thereof, and/or the like.

According to the invention described herein, said at least one viscosity modifying agent may be a synthetic polymer, a semi-synthetic polymer or a synthetic rubber, selected from the group comprising, but not limited to:
  carboxyvinyl polymers; polyvinylpyrrolidone (povidone); polyvinyl alcohol; polyvinyl acetates, polyvinyl chlorides, polyvinylidenes, and/or the like;
  polymers and copolymers of methacrylic acid;
  cellulose derivatives, comprising, but not limited to: methyl cellulose, hydroxypropyl cellulose, hydroxypropylmethyl cellulose, hydroxyethyl cellulose, hydroxypropylmethyl cellulose, methyl hydroxyethyl cellulose, methyl hydroxypropyl cellulose, carboxymethyl hydroxyethyl cellulose, carboxymethyl cellulose, sodium carboxymethyl cellulose, and/or the like;
  carbomers (cross-linked homopolymers or copolymers of acrylic acid), commercially known with the trade name Carbopol®, such as Carbopol® 980, Carbopol® 934, Carbopol® 940, Carbopol® 941, Carbopol® 981, and/or the like;
  polyethylene glycol derivatives in various degrees of polymerization, such as PEG 1000, PEG 3350, PEG 4000, PEG 6000, PEG 10000.

Any mixture of the viscosity modifying agents mentioned above may be used to form the appropriate composition. According to an embodiment, said at least one viscosity modifying agent is hydroxypropyl cellulose. According to another embodiment, the at least one viscosity modifying agent is PEG 6000 (polyethylene glycol 6000). According to a preferred embodiment, said at least one viscosity modifying agent is a carbomer, preferably carbomer 980 (commercially known with the trade name Carbopol® 980). According to a further preferred embodiment, said at least one viscosity modifying agent is hydroxypropyl cellulose.

According to a still further preferred embodiment, said at least one viscosity modifying agent is polyvinylpyrrolidone (povidone).

According to the invention described herein, said at least one viscosity modifying agent is contained in an amount ranging from about 0.1 g/100 ml to about 20.0 g/100 ml (from about 0.1% w/v to about 20.0% w/v), preferably from about 0.5 g/100 ml to about 10.0 g/100 ml (from about 0.5% w/v to about 10.0% w/v), more preferably from about 1.0 g/100 ml to about 5.0 g/100 ml (from about 0.5% w/v to about 5.0% w/v). According to an embodiment, said at least one viscosity modifying agent is contained in an amount of about 1.0 g/100 ml (about 1.0% w/v). According to an embodiment, said at least one viscosity modifying agent is contained in an amount of about 1.5 g/100 ml (about 1.5% w/v). According to an embodiment, said at least one viscosity modifying agent is contained in an amount of about 2.0 g/100 ml (about 2.0% w/v). According to an embodiment, said at least one viscosity modifying agent is contained in an amount of about 3.0 g/100 ml (about 3.0% w/v). According to an embodiment, said at least one viscosity modifying agent is contained in an amount of about 5.0 g/100 ml (about 5.0% w/v).

According to the invention described herein, said emulsion or microemulsion oily phase comprises at least one lipophilic compound. Said at least one lipophilic compound is preferably selected from the group comprising, but not limited to: natural oils such as almond oil, hydrogenated castor oil, almond oil, olive oil, cottonseed oil, soybean oil, linseed oil, peanut oil, sesame oil and/or the like; fatty alcohols such as oleic alcohol, myristic alcohol and/or the like; fatty acid esters, such as cetyl palmitate, isopropyl myristate, isopropyl palmitate, ethyl oleate and/or the like; fatty acids, such as myristic acid, oleic acid and/or the like; paraffin; light mineral oil; heavy mineral oil; triglycerides, such as long and/or medium-chain triglycerides and/or the like; medium-chain triglycerides (commercially known under the trade name Labrafac™ Lipophile WL1349); diglycerides; monoglycerides; silicone derivatives, simethicone, 30% simethicone emulsion and/or the like. Any mixture of the lipophilic compounds mentioned above may be used to prepare the appropriate composition. According to an embodiment, said at least one lipophilic compound is soybean oil. According to another embodiment, said at least one lipophilic compound is oleic alcohol. According to an embodiment, said at least one lipophilic compound is isopropyl myristate. According to an embodiment, said at least one lipophilic compound is castor oil. According to a preferred embodiment, said at least one lipophilic compound is a mixture of medium chain triglycerides (commercially known under the trade name Labrafac™ Lipophile WL1349). According to another preferred embodiment, said at least one lipophilic compound is 30% simethicone emulsion. According to the invention described herein, said at least one lipophilic compound is contained in the composition in the form of an emulsion or microemulsion in an amount ranging from about 0.05 g/100 ml to about 10.0 g/100 ml (from about 0.05% w/v to about 10.0% w/v), preferably from about 0.1 g/100 ml to about 5.0 g/100 ml (from about 0.1% w/v to about 5.0% w/v). According to an embodiment, said at least one lipophilic compound is contained in an amount of about 0.1 g/100 ml (about 0.1% w/v). According to an embodiment, said at least one lipophilic compound is contained in an amount of about 0.5 g/100 ml (about 0.5% w/v). According to another embodiment, said at least one lipophilic compound is contained in an amount of about 1.0 g/100 ml (about 1.0% w/v). According to another embodiment, said at least one lipophilic compound is contained in an amount of about 2.0 g/100 ml (about 2.0% w/v). According to another embodiment, said at least one lipophilic compound is contained in an amount of about 3.0 g/100 ml (about 3.0% w/v). According to another embodiment, said at least one lipophilic compound is contained in an amount of about 5.0 g/100 ml (about 5.0% w/v). As above, the amounts are expressed in grams per 100 ml of liquid composition in the form of an emulsion or microemulsion, or in percentage weight/volume of the composition.

In addition, the composition may contain at least one inverse thermosensitive polymer. As well known in the art, the inverse thermosensitive polymers are polymers that, after dissolution in a solvent (such as water) in a concentration above the critical micelle concentration (CMC), have the tendency to form micelles. At concentrations above the critical gelation concentration (CGC), these micelles can be ordered in a lattice; the result is a solution that has characteristics of inverse viscosity, which means that the solution shows an increase in its viscosity with temperature. Eventually, when the temperature is increased above the critical gelation temperature (CGT), a gel is formed. Gelling is due to a physical rearrangement and to packing of the micellar structures, and it is reversible, therefore the gel returns to a liquid form when the temperature is lowered below the critical gelation temperature. Polymers of this type are well known in the art and include, for example, poloxamers (marketed by BASF under the trade name Kolliphor™) and poloxamine (marketed by BASF under the trade name Tetronic™).

According to an embodiment, said at least one inverse thermosensitive polymer is contained at a concentration equal to or greater than the critical gelation concentration (CGC). According to this embodiment, said liquid composition in the form of an emulsion or microemulsion is characterized by a critical gelation temperature (CGT), i.e., a temperature at which the transition occurs from a liquid state to a gel state.

According to another embodiment, said at least one inverse thermosensitive polymer is contained at a concentration below the critical gelation concentration (CGC). According to this embodiment, said liquid composition in the form of an emulsion or microemulsion has no gelling capacity.

The gelling capacity of inverse thermosensitive polymers solutions requires that the concentration of said polymer in said solutions is equal to or higher than the critical gelation concentration (CGC): solutions of said polymers form gels above the critical gelation concentration (CGC), when the temperature is increased above the critical gelation temperature (CGT).

The critical gelation temperature (CGT) can be modulated by varying the concentration of the inverse thermosensitive polymer, which means that the higher the concentration of said polymer, the lower the critical gelation temperature (CGT). The type of inverse thermosensitive polymer used in the preparation of such a composition, as well as its concentration, has an impact on the CGT. In the preparation of liquid compositions in the form of an emulsion or microemulsion according to the invention described herein, the choice of the appropriate inverse thermosensitive polymers, and their concentrations, may be made to obtain a final composition that is in the liquid state below the body temperature (i.e., below about 37° C.) and that it becomes a gel when heated at or above the body temperature (i.e., at or above about 37° C.). In this case, the composition in form of an emulsion or microemulsion according to the invention described herein is able to modify its physical characteristics after the administration in the target organs, because of the different temperature between the place where the composition is administered (for example the temperature of the room of the diagnostic center, or other suitable place of administration), and the body temperature (usually about T=37° C.). After the liquid composition in the form of an emulsion or microemulsion of the invention, comprising also said at least one inverse thermosensitive polymer at a concentration higher than the CGC, comes into contact with the warm walls of the mucosa, its viscosity increases thus increasing the adhesion of the composition on the target organs.

According to the invention described herein, said at least one inverse thermosensitive polymer may be selected from the group comprising, but not limited to: block copolymers of polyoxyethylene-polyoxypropylene, such as poloxamer 124, poloxamer 188, poloxamer 237, poloxamer 338, poloxamer 407 and/or the like. Any mixture of the inverse thermosensitive polymers mentioned above may be used to form the appropriate composition. In one embodiment, said at least one inverse thermosensitive polymer is poloxamer 188. In a preferred embodiment, said at least one inverse thermosensitive polymer is poloxamer 407. In yet another preferred embodiment, said at least one inverse thermosensitive polymer comprises a mixture of poloxamer 188 and poloxamer 407.

According to an embodiment, said at least one inverse thermosensitive polymer is contained in an amount equal to or greater than the CGC (critical gelling concentration). According to this embodiment, the concentration of said at least one inverse thermosensitive polymer is selected to obtain a critical gelation temperature (CGT) higher than the room temperature (i.e., higher than about 20°-25° C.), preferably close to the body temperature (i.e., is about 37° C.). According to the above embodiment, a preferred critical gelation temperature (CGT) of said pharmaceutical composition in the form of an emulsion or microemulsion is below 45° C., preferably between 10° C. and 43° C., more preferably between 20° C. and 40° C.

According to another embodiment, said at least one inverse thermosensitive polymer is contained in an amount below the CGC (critical gelling concentration). According to this embodiment, the pharmaceutical composition in the form of an emulsion or microemulsion is in the liquid phase up to a temperature of about 40° C. in test laboratory condition, preferably both at room temperature (i.e., about 20-25° C.) and at body temperature (i.e., about 37° C.) in test laboratory condition. According to the above embodiment, said pharmaceutical composition in the form of an emulsion or microemulsion is not able to change from a liquid phase to a gel phase in response to an increase in temperature of up to 40° C., such as from room temperature (i.e., about 20-25° C.) to body temperature (i.e., about 37° C.).

According to the invention described herein, said at least one inverse thermosensitive polymer is contained in the liquid composition in the form of an emulsion or a microemulsion in an amount ranging from about 1.0 g/100 ml to about 40.0 g/100 ml (from about 1.0% w/v to about 40.0% w/v), preferably from about 2.0 g/100 ml to about 30.0 g/100 ml (from about 2.0% w/v to about 30.0% w/v), more preferably from about 5.0 g/100 ml to about 25.0 g/l 00 ml (from about 5.0% w/v to about 25.0% w/v). According to an embodiment, said at least one inverse thermosensitive polymer is poloxamer 407 and it is contained in an amount of about 5.0 g/100 ml (about 5.0% w/v). According to an embodiment, said at least one inverse thermosensitive polymer is poloxamer 338 and it is contained in an amount of about 10.0 g/100 ml (about 10.0% w/v). According to an embodiment, said at least one inverse thermosensitive polymer is poloxamer 407 and it is contained in an amount of about 10.0 g/100 nil (about 10.0% w/v). According to an embodiment, said at least one inverse thermosensitive polymer is poloxamer 407 and it is contained in an amount of about 12.0 g/100 ml (about 12.0% w/v). According to an embodiment, said at least one inverse thermosensitive polymer is poloxamer 407 and it is contained in an amount of about 13.0 g/100 ml (about 13.0% w/v). According to an embodiment, said at least one inverse thermosensitive polymer is poloxamer 407 and it is contained in an amount of about 13.2 g/100 ml (about 13.2% w/v). According to an embodiment, said at least one inverse thermosensitive polymer is poloxamer 407 and it is contained in an amount of about 15.0 g/100 ml (about 15.0% w/v). According to an embodiment, said at least one inverse thermosensitive polymer is poloxamer 188 and it is contained in an amount of about 15.0 g/100 ml (about 15.0% w/v). According to an embodiment, said at least one inverse thermosensitive polymer is poloxamer 188 and it is contained in an amount of about 20.0 g/100 ml (about 20.0% w/v). According to an embodiment, said at least one inverse thermosensitive polymer is poloxamer 188 and it is contained in an amount of about 25.0 g/100 ml (about 25.0% w/v). According to an embodiment, said at least one inverse thermosensitive polymer is poloxamer 188 and it is contained in an amount of about 30.0 g/100 ml (about 30.0% w/v). According to an embodiment, said at least one inverse thermosensitive polymer is poloxamer 188 and it is contained in an amount of about 35.0 g/100 ml (about 35.0% w/v).

According to an embodiment, said at least one inverse thermosensitive polymer consists of a mixture of poloxamer 407 and poloxamer 188, and said poloxamer 407 and poloxamer 188 are contained in an amount of about 12.4 g/100 ml (about 12.4% w/v) and of about 7.8 g/100 ml (about 7.8% w/v), respectively. According to an embodiment, said at least one inverse thermosensitive polymer consists of a mixture of poloxamer 407 and poloxamer 188, and said poloxamer 407 and poloxamer 188 are contained in an amount of about 13.2 g/100 ml (about 13.2% w/v) and of about 7.8 g/100 ml (about 7.8% w/v), respectively. According to an embodiment, said at least one inverse thermosensitive polymer consists of a mixture of poloxamer 407 and poloxamer 188, and said poloxamer 407 and poloxamer 188 are contained in an amount of about 14.0 g/100 ml (about 14.0% w/v) and of about 7.8 g/100 ml (about 7.8% w/v), respectively. According to an embodiment, According to an embodiment, said at least one inverse thermosensitive polymer consists of a mixture of poloxamer 407 and poloxamer 188, and said poloxamer 407 and poloxamer 188 are contained in an amount of about 15.0 g/100 ml (about 15.0% w/v) and of about 10.0 g/100 ml (about 10.0% w/v), respectively. According to an embodiment, According to an embodiment, said at least one inverse thermosensitive polymer consists of a mixture of poloxamer 407 and poloxamer 188, and said poloxamer 407 and poloxamer 188 are contained in an amount of about 16.0 g/100 ml (about 16.0% w/v) and of about 10.0 g/100 ml (about 10.0% w/v), respectively. According to an embodiment, According to an embodiment, said at least one inverse thermosensitive polymer consists of a mixture of poloxamer 407 and poloxamer 188, and said poloxamer 407 and poloxamer 188 are contained in an amount of about 17.0 g/100 ml (about 17.0% w/v) and of about 10.0 g/100 ml (about 10.0% w/v), respectively.

According to the invention described herein, said liquid composition in the form of an emulsion or microemulsion may comprise at least one inorganic salt, at least one organic salt or a mixture thereof. In some embodiments of the invention described herein, said liquid composition in the form of an emulsion or microemulsion may comprise one or more inorganic salts selected from the group comprising, but not limited to: chlorides, bromides, iodides, phosphates, carbonates, bicarbonates, sulfates, nitrates, silicates and/or the like. In some embodiments, said liquid composition in the form of an emulsion or microemulsion may comprise one or more organic salts selected from the group comprising, but not limited to: citrates, maleates, fumarates, acetates, lactates and/or the like. Any mixture of the above inorganic and organic salts may be used to form the appropriate composition, generally to buffer the pH of the composition in appropriate biocompatible ranges, or to reach the osmotic pressure required by the biological environment where said pharmaceutical composition is to be administered.

Preferably, the inorganic and/or organic salts used are sodium dihydrogen phosphate anhydrous, dibasic sodium phosphate anhydrous, sodium chloride, or mixtures thereof.

Said at least one inorganic salt, organic salt, or mixture thereof, is contained in the composition of the invention in an amount ranging about 0 g/l 00 ml to about 20.0 g/100 ml (from about 0% w/v to about 20.0% w/v), preferably from about 0.5 g/100 ml to about 10.0 g/100 ml (from about 0.5% w/v to about 10.0% w/v).

Finally, the liquid composition in the form of an emulsion or microemulsion of the present invention may also contain at least one preservative, preferably selected from the group comprising, but not limited to: benzoic acid, sodium benzoate, potassium benzoate, calcium benzoate, p-hydroxybenzoic acid, sodium p-hydroxybenzoate, methyl p-hydroxybenzoate, ethyl p-hydroxybenzoate, propyl p-hydroxybenzoate, butyl p-hydroxybenzoate, salicylic acid, cresol, cetrimide, potassium sorbate, sorbic acid, benzalkonium chloride, benzyl alcohol, chlorobutol, phenol, chlorocresol, phenylmercuric salts, bronopol, cetylpyridinium chloride, chloroxylenol, ethyl alcohol, glycerin, hexetidine, imidurea, phenoxyethanol, phenylethyl alcohol, propylene glycol, thimerosal, sodium propionate, benzethonium chloride. Any mixture of the preservatives mentioned above can be used to form the appropriate composition. Preferably, the preservatives used are sodium benzoate, methyl p-hydroxybenzoate or mixtures thereof.

Said at least one preservative, or mixture of preservative, is contained in the composition of the invention in amounts ranging from about 0.01 g/100 ml to about 5M g/100 ml (from about 0.01% w/v to about 5.0% w/v), preferably from about 0.02 g/100 ml to about 2.0 g/100 ml (from about 0.02% w/v to about 2.0% w/v), more preferably from about 0.05 g/100 ml to about 1.0 g/100 ml (from about 0.05% w/v to about 1.0% w/v).

As above, the amounts are expressed in grams per 100 ml of liquid composition in the form of an emulsion or microemulsion, or in percentage weight/volume of the composition.

In addition, other physiologically acceptable excipients may be added to the composition in the form of an emulsion or microemulsion according to the invention described herein, to obtain a final composition for use in diagnostic endoscopic procedures of sigmoid colon and/or rectum, provided with appropriate characteristics and stability. By way of example, these physiologically acceptable excipients may be selected from excipients well known in the art, such as antioxidants, chelating agents, solvents and/or the like.

The liquid composition in the form of an emulsion or microemulsion of the invention is preferably formulated in the form of clyster (also clistere or enema) and/or washing solution (in the form of an emulsion or microemulsion).

In addition to the increased absorption of the dye discussed above, the particular formulation of the emulsion or microemulsion of the invention also ensures a reduced tendency to flow along the walls of the mucosae, when compared to known solutions commonly used in this technical field (for example aqueous solutions); as a result, the dye dissolved in it remains in contact with the cell membrane of the epithelial cells of the mucosa for a period of time longer than the dye dissolved in a simple solution. These features are particularly advantageous when the liquid composition of the present invention contains a vital dye (or "absorptive"), such as methylene blue or toluidine blue or Lugol's solution.

These types of dyes must in fact be absorbed by the cells to exert their staining properties. The longer a vital dye remains in contact with the cell membrane, the greater is the amount of dye that can be absorbed by the epithelial cells, and the greater is the staining effect obtained and the visualized contrast during the endoscopic diagnosis.

In this way, the composition of the invention may also provide an identification of pathological formations, of benign or malignant tissue or of disorders of the area covered by the analysis in an early and effective way, thus limiting the undesired development of diseases because of their difficult visualization. For example, an early visualization and diagnosis of neoplastic masses of the sigmoid colon and/or rectum, even when they are of minimal size (mm), may be curative or at least important for the assessment of the therapy, or of a possible surgery. The same reasoning may naturally be applied in case of polyps, flat polyps, pseudo-polyps, dysplasias, and tightened injury.

The liquid composition in the form of an emulsion or microemulsion of the present invention is therefore suitable for diagnostic use, preferably in the diagnostic endoscopic evaluation of sigmoid colon and/or rectum, and more preferably in anoscopy, proctoscopy, sigmoidoscopy and/or rectoscopy.

The endoscopic diagnostic evaluation of the present invention is then preferably directed to the identification of several pathological and/or non-pathological forms of the intestinal mucosa, preferably at the level of the sigmoid colon and/or rectum. More preferably, said pathological and/or non-pathological forms comprise, but are not limited to: inflammatory lesions, ulcers, polyps, pseudo-polyps, flat polyps, hyperplastic polyps, tightened lesions, adenomas, pre-neoplastic formations, neoplastic formations, tumors and/or carcinoma.

The composition of the invention is then administered rectally, preferably during the preparation phase of the diagnostic endoscopic investigation. As well known in the art, the preparation phase is a critical step to be performed before the diagnostic endoscopic examination, especially in case of anoscopy, proctoscopy, sigmoidoscopy and/or rectoscopy, where the purpose of said preparatory phase is essentially to cleanse the lower colon from residual fecal material or feces to enable the doctor to see the walls of sigmoid colon and/or rectum mucosa. This preparation phase usually begins 24 hours before the diagnostic procedure, when the subject must start a liquid based diet. The preparation kits are available in pharmacies. Usually, about 20 hours before the exam, the subject begins to take laxatives, which can be oral tablets or liquid formulations. The subject must stop taking any type of liquid 4 hours before the exam. One or two hours before the exam, the subject uses an enema or laxative suppositories to finish cleansing the lower intestine.

According to an embodiment, the liquid composition in the form of an emulsion or microemulsion of the invention is capable of both cleansing the sigmoid colon and/or rectum from fecal residue, feces and/or mucus (evacuation property) and of staining in an optimal and prolonged way the mucosa walls.

The effective cleansing and staining act in a combined way in order to ensure an optimal visualization of the mucosa during the diagnostic endoscopic procedure, especially of the sigmoid colon and/or rectum.

According to this embodiment, the composition is administered rectally, preferably from three hours up to 30 minutes before the diagnostic endoscopic examination and provides the dual activity mentioned above: both the evacuative activity, with cleansing of the lower colon from the feces; and the improved staining activity of the sigmoid colon and/or rectum mucosa prior to analysis.

According to another embodiment, the liquid composition in the form of an emulsion or microemulsion of the invention has staining but not evacuative properties. According to this embodiment, the composition of the invention is administered rectally from 3 hours before to a few minutes before the diagnostic endoscopic examination, so as to act solely as a preparation for the staining of the sigmoid colon and/or rectum mucosa, without acting as a preparation for cleansing. According to this embodiment, the composition of the invention is therefore preferably administered after a proper cleansing of the colon, in particular the lower colon, which is carried out with known preparations as, for example, Selg Esse 1000®, Phospho-Lax®, Iscolan®, Clisalmax®, Klean-Prep®. In this case, with no fecal residual remaining in the lower colon, it is possible to better appreciate the staining action of the composition, as fecal residues could absorb a part of the dye contained in the composition. According to this embodiment, the liquid composition in the form of an emulsion or microemulsion according to the invention described herein may be combined with a laxative clyster (also clistere or enema) known in the art, to form a kit for use in an endoscopic procedure of the sigmoid colon and/or rectum, wherein said endoscopic procedure of sigmoid colon and/or rectum is preferably an anoscopy, a proctoscopy, a rectoscopy and/or a sigmoidoscopy. Therefore, a further aspect of the invention described herein provides a kit that includes:
  the liquid composition in the form of an emulsion or microemulsion according to the invention described herein;
  a laxative enema;
  instructions for use.

The kit of the invention is preferably suitable for use in a diagnostic endoscopic procedure of the sigmoid colon and/or rectum, more preferably in an anoscopy, in a proctoscopy, in a rectoscopy and/or in a sigmoidoscopy.

In one embodiment, in the preparation of said kit, the laxative enema can be formulated according to qualitative-quantitative compositions well known in the art.

In another embodiment, in the preparation of said kit, the laxative enema may be selected from laxative enemas approved for human use and available on the market, said group comprising, but not limited to: Clisflex®, Clisma Fleet®, Clisma Lax®, Enemax®, Glicerolax®, Macrolax®, Verolax® and the like.

DEFINITIONS

In the specification, references to "one embodiment", "the embodiment", and the like, indicate that the described embodiment may include a particular aspect, feature, structure or characteristic. Furthermore, these phrases may, but not necessarily, refer to the same embodiment to which it is referred to in other portions of the specification. Also, when a particular aspect, feature, structure or characteristic is described in connection with one embodiment, it falls within the knowledge of one skilled in the art to modify or connect said aspect, feature, structure or characteristic with other embodiments, whether explicitly described or not.

The singular forms "a", "an" and "the" include plural references, unless the context clearly requires otherwise. Thus, for example, a reference to "a compound" includes a plurality of such compounds. It has also to be noted that the claims may be drafted to exclude any optional element. As such, this statement is intended to provide the antecedent basis for the use of exclusive terminology such as "solely," "only" and the like, in connection with the recitation of claims elements, or use of a "negative" restriction.

The term "and/or" means any of the items, any combination of the items, or all the items associated with this term.

The terms "comprising", "having", "including" and "containing" are to be understood as open terms (i.e., meaning "comprising, but not limited to"), and are to be considered as a support also for terms such as "consists essentially of", "consisting essentially of", "consists of" or "consisting of". The terms "consists essentially of", "consisting essentially of" are to be understood as semi-closed terms, which means that any other ingredient that affects the basic characteristics and novelty of the invention is not included.

The terms "consists of", "consisting of" are defined as closed terms.

Unless otherwise indicated herein, the term "about" is understood to include values, for example weight percentages, in the proximity of the range listed that, in terms of functionality of the individual component, of the composition, or the realization, are equivalent.

One skilled in the art will recognize that, for any and all purposes, particularly in terms of providing a written description, all ranges mentioned in this specification also include any and all possible sub-ranges and combinations of their sub-ranges, as well as all the individual values in the range, particularly integer values. A range listed includes each specific value, integer, decimal, or identity within the range.

One skilled in the art will recognize that, where there are members grouped together in a common way, such as in a Markush group, the invention comprises not only the entire group listed as a whole, but each member of the group individually and all possible subgroups of the main group. Moreover, for all purposes, the invention includes not only the main group, but also the main group in the absence of one or more of the group members. The invention therefore provides for the explicit exclusion of one or more members of a group listed. Therefore, conditions may apply to one or more of the categories or embodiments described, in which one or more of the listed items, the species, or the implementations, may be excluded from these categories or embodiments, for example, as used in an explicit negative limitation.

The term "emulsion" refers to a heterogeneous preparation comprised of two immiscible liquids (by convention, described as oil and water), one of which is uniformly dispersed as fine droplets in the other. The phase present as small droplets is called the dispersed phase, dispersed, or internal phase, and the carrier liquid is known as the continuous or external phase. The emulsions are conveniently classified as oil-in-water (o/w) or water-in-oil (w/o), depending on whether the continuous phase is aqueous or oily. Multiple emulsions, which are prepared from oil and water by means of a re-emulsification of a pre-existing emulsion to form two dispersed phases, are also of pharmaceutical interest. Multiple emulsions of the type "oil-in-water-in-oil" (o/w/o) are w/o emulsions in which the same water droplets contain dispersed oil droplets; on the contrary, emulsions "water-in-oil-in-water" (a/o/a) are those where the internal and external aqueous phases are separated from the oil. The "microemulsions" are dispersions of oil and water thermodynamically stable, transparent (or translucent) which may be stabilized by an interfacial film of surfactant molecules. The surfactant can be pure, a mixture, or a combination with a co-surfactant, such as a medium chain alcohol. The microemulsions are easily distinguished from the normal emulsions for their transparency, their low viscosity, and more fundamentally for their thermodynamic stability and their ability to form spontaneously. The above definitions of "emulsion" and "microemulsion" were taken from "Emulsion and microemulsion", Encyclopedia of Pharmaceutical Technology, 3rd Edition, Informa Healthcare.

"Viscosity" defines the resistance to flow of a liquid or semisolid. The liquid or semi-solid flow is described by the viscosity, or, more precisely, by the shear viscosity $\eta$. The shear viscosity of a fluid expresses its resistance to the shear flow, in which the adjacent layers move parallel to each other at different speeds. Common unit of measurement of the viscosity is the Pascal-second (Pa s), the poise (P), and the centipoise "cP".

"Body temperature" refers to the level of heat produced and supported by the body processes. The heat is generated within the body through the metabolism of nutrients, and it is dispersed from the surface of the body by radiation, convection, and sweat evaporation. Production and heat loss are regulated and controlled by the hypothalamus and the brain stem. The normal temperature of the adult body, measured orally, is 37° C., although small variations are usually recorded during the day.

The "room temperature" (RT) is generally defined as the temperature of the environmental air in any room used for a given procedure. More specifically, it is defined as 20-25° C., since some ambient temperatures, by nature, do not fall in this range. Usually, protocols that require steps to be performed at RT require temperatures not falling below 18° C., and not exceeding 27° C.

For a composition containing a inverse thermosensitive polymer, the "critical gelling concentration" (CGC), represents the concentration of said polymer above which said composition is able to change from a liquid phase to a gel phase in response to a temperature increase.

The "critical gelation temperature" (CGT) represents the temperature above which a composition containing a inverse thermosensitive polymer, at a concentration equal to or greater than the critical gelling concentration, changes from a liquid phase to a gel phase.

"Lugol's solution" is a solution of elemental iodine and potassium iodide in water.

"cP" centipoise, unit of measurement of the viscosity.

The following examples are included for illustration purposes of certain aspects and embodiments of the invention, and are not intended to limit the invention

EXAMPLES

Example 1

| Component | Unit of Measure | Amount for 100 ml |
|---|---|---|
| Methylene blue | g | 0.04 |
| Sodium dihydrogen phosphate, anhydrous | g | 0.70 |
| Dibasic sodium phosphate, anhydrous | g | 0.15 |
| Sodium hydroxide | g | 0.06 |
| Caprylocaproyl macrogol-8 glycerides (Labrasol ®) | g | 5.00 |
| Medium chain triglycerides (Labrafac ® Lipophile WL1349) | g | 1.00 |
| Diethylene glycol monoethyl ether (Transcutol ®) | g | 5.00 |
| Carbomer 980 (Carbopol ® 980) | g | 1.50 |
| Sodium benzoate | g | 0.10 |
| Methyl p-hydroxybenzoate | g | 0.10 |
| Purified water | ml | q.b. a 100 |

Sodium dihydrogen phosphate anhydrous (7.0 g), dibasic sodium phosphate anhydrous (1.5 g), sodium hydroxide (0.6 g), Transcutol® (50.0 g), sodium benzoate (1.0 g) and methyl p-hydroxybenzoate (1.0 g) are added to 850 ml of purified water, in a dissolutor equipped with a mechanical stirrer. Stirring is maintained until a homogeneous mixture is obtained.

The stirring rate is set at 800 rev/min, and Carbopol® 980 (15.0 g), Labrasol® (50.0 g) and Labrafac® Lipophile WL1349 (10.0 g) are added under stirring. The mixture obtained is filtered on high porosity filter paper, and the volume brought to the final value (1000 ml) with purified water. Methylene blue (0.5 g, equivalent to about 0.4 g of anhydrous substance) is added. The mixture is maintained under stirring until complete dissolution of the methylene blue.

Example 2

| Component | Unit of Measure | Amount for 100 ml |
|---|---|---|
| Methylene blue | g | 0.020 |
| Poloxamer 407 (Kolliphor ® P407) | g | 15.00 |
| Diethylene glycol monoethyl ether (Transcutol ®) | g | 5.00 |
| Sodium benzoate | g | 0.10 |
| Methyl p-hydroxybenzoate | g | 0.10 |
| 30% simethicone emulsion | g | 0.10 |
| Caprylocaproyl macrogol-8 glycerides (Labrasol ®) | g | 1.00 |
| Purified water | ml | q.b. a 100 |

A dissolutor is charged with purified water (3.400 Kg); it is placed under stirring with a mechanical stirrer at a temperature T<20° C. 30% simethicone emulsion (0.005 Kg) and Kolliphor® P407 (0.750 Kg) are added. Stirring is maintained at a temperature T<20° C. until a homogeneous mixture is obtained (about 90 minutes) (Mixture A).

Another dissolutor is charged with purified water (0.500 Kg); it is placed under stirring with a mechanical stirrer at room temperature. Sodium benzoate (0.005 Kg) is added.

Stirring is maintained until a homogeneous mixture is obtained (about 10 minutes) (Mixture B).

Mixture B is added to Mixture A under stirring at room temperature; stirring is maintained until a homogeneous mixture is obtained (Mixture C).

Labrasol® (0.050 Kg) is added to Mixture C under stirring at room temperature; stirring is maintained until a homogeneous mixture is obtained (Mixture D).

A dissolutor is charged with Transcutol® (0.250 Kg); it is placed under stirring with a mechanical stirrer at room temperature. Methyl p-hydroxybenzoate (0.005 Kg) is added. Stirring is maintained until a homogeneous mixture is obtained (about 10 minutes) (Mixture E).

Mixture E is added to Mixture D in the dissolutor under stirring at room temperature Stirring is maintained until a homogeneous mixture is obtained (Mixture F).

A dissolutor is charged with purified water (0.500 Kg); it is placed under stirring with a mechanical stirrer at room temperate. Methylene blue (1.200 g, equivalent to about 1.000 g di anhydrous substance) is added. Stirring is maintained until a homogeneous mixture is obtained (about 10 minutes) (Mixture G).

Mixture G is added to Mixture F under stirring at room temperature. It is brought to final volume (V=5.00 l) with purified water.

The composition thus obtained has the following characteristics:

| | |
|---|---|
| pH | 6.9; |
| Density | 1.007 g/ml; |
| Viscosity at T = 20.0° C. ± 0.1° C. | 65.8 cP; |
| Viscosity at T = 37.0° C. ± 0.1° C. | 24739 cP. |

Example 3

| Component | Unit of Measure | Amount for 100 ml |
|---|---|---|
| Methylene blue | g | 0.02 |
| Propylene glycol monocaprylate (Capryol ® 90) | g | 1.50 |
| Caprylocaproyl macrogol-8 glycerides (Labrasol ®) | g | 10.00 |
| Lauroyl macrogol-32 glycerides (Gelucire ® 44/14) | g | 8.00 |
| Sodium benzoate | g | 0.10 |
| Methyl p-hydroxybenzoate | g | 0.10 |
| 30% simethicone emulsion | g | 1.00 |
| Purified water | ml | q.b. a 100 |

A dissolutor is charged with purified water (6.000 Kg); it is placed under stirring with a mechanical stirrer at room temperature. Methyl p-hydroxybenzoate (0.008 Kg) is added, while keeping under stirring and gradually increasing the temperature up to a final value T=80° C. Stirring is maintained, at a temperature T=80° C., until a clear solution is obtained. It is cooled to a temperature T=40° C. while keeping under stirring. Sodium benzoate (0.008 Kg), 30% simethicone emulsion (0.080 Kg), Capryol® 90 (0.120 Kg) and Labrasol® (0.800 Kg) are added under stirring at T=40° C. Stirring is maintained for about 20 minutes at T=40° C. (Mixture A).

Gelucire® 44/14 (0.640 Kg) is heated to a temperature T=40° C. in a suitable container. The melt thus obtained is added to Mixture A, under stirring at T=40° C. Stirring is maintained for about 20 minutes at T=40° C.; it is brought back to room temperature (Mixture B).

Methylene blue (1.92 g, equivalent to about 1.60 g of anhydrous substance) is added to Mixture B, under stirring at room temperature. Stirring is maintained for about 20 minutes at room temperature. It is brought to final volume (V=8.00 l) with purified water.

The composition thus obtained has the following characteristics:

| | |
|---|---|
| pH | 5.8; |
| Density | 1.015 g/ml. |

Example 4

| Component | Unit of Measure | Amount for 100 ml |
|---|---|---|
| Indigo carmine | g | 0.04 |
| Sodium dihydrogen phosphate, anhydrous | g | 13.90 |
| Dibasic sodium phosphate, anhydrous | g | 3.18 |
| Sodium hydroxide | g | 0.12 |
| Caprylocaproyl macrogol-8 glycerides (Labrasol ®) | g | 10.00 |
| Diethylene glycol monoethyl ether (Transcutol ®) | g | 10.00 |
| Sodium benzoate | g | 0.10 |
| Methyl p-hydroxybenzoate | g | 0.10 |
| Purified water | ml | q.b. a 100 |

Sodium dihydrogen phosphate anhydrous (139.0 g), dibasic sodium phosphate anhydrous (31.8 g), sodium hydroxide (1.2 g), Transcutol® (100.0 g), sodium benzoate (1.0 g) and methyl p-hydroxybenzoate (1.0 g) are added to 700 ml of purified water in a dissolutor equipped with mechanical stirring. Stirring is maintained until a homogeneous solution is obtained.

The stirring rate is set at 800 rev/min, and Labrasol® (100.0 g) is added under stirring. The mixture obtained is filtered on high porosity filter paper, and the volume brought to the final value (1000 ml) with purified water. Indigo carmine (0.588 g, equivalent to about 0.400 g of anhydrous substance) is added. The mixture is maintained under stirring until complete dissolution of the dye.

Example 5

| Component | Unit of Measure | Amount for 100 ml |
|---|---|---|
| Methylene blue | g | 0.04 |
| Polysorbate 80 (Tween ® 80) | g | 10.00 |
| Diethylene glycol monoethyl ether (Transcutol ®) | g | 10.00 |
| Poloxamer 407 (Kolliphor ® P407) | g | 5.00 |
| Ethyl oleate | g | 1.00 |
| Sodium benzoate | g | 0.10 |
| Methyl p-hydroxybenzoate | g | 0.10 |
| Purified water | ml | q.b. a 100 |

Transcutol® (100.0 g), Tween® 80 (100.0 g), ethyl oleate (10.00 g), sodium benzoate (1.0 g) and methyl p-hydroxybenzoate (1.0 g) are added to 700 ml of purified water in a dissolutor equipped with mechanical stirring. Stirring is maintained until a homogeneous solution is obtained.

The stirring rate is set at 800 rev/min, and Kolliphor® P407 (50.0 g) is added under stirring. The mixture obtained is filtered on high porosity filter paper, and the volume brought to the final value (1000 ml) with purified water. Methylene blue (0.5 g, equivalent to about 0.4 g of anhydrous substance) is added. The mixture is maintained under stirring until complete dissolution of the methylene blue.

Example 6

| Component | Unit of Measure | Amount for 100 ml |
|---|---|---|
| Indigo carmine | g | 0.01 |
| Sodium citrate | g | 5.00 |
| Potassium tartrate | g | 5.00 |
| Polyethylene glycol 40 stearate (Myrj ™ S40) | g | 10.00 |
| Caprylocaproyl macrogol-8 glycerides (Labrasol ®) | g | 10.00 |
| Glycerol | g | 5.00 |
| Carbomer 980 (Carbopol ® 980) | g | 1.50 |
| Soybean oil | g | 0.50 |
| Sodium benzoate | g | 0.10 |
| Methyl p-hydroxybenzoate | g | 0.10 |
| Purified water | ml | q.b. a 100 |

Sodium citrate (50.0 g), potassium tartrate (50.0 g), glycerol (50.0 g), Myrj™ S40 (100.0 g), Labrasol® (100.0 g), soybean oil (5.00 g), sodium benzoate (1.0 g) and methyl p-hydroxybenzoate (1.0 g) are added to 850 ml of purified water in a dissolutor equipped with mechanical stirring. Stirring is maintained until a homogeneous solution is obtained.

The stirring rate is set at 800 rev/min, and Carbopol® 980 (15.0 g) is added under stirring. The mixture obtained is filtered on high porosity filter paper, and the volume brought to the final value (1000 ml) with purified water. Indigo carmine (0.118 g, equivalent to about 0.100 g of anhydrous substance) is added. The mixture is maintained under stirring until complete dissolution of the indigo carmine.

Example 7

| Component | Unit of Measure | Amount for 100 ml |
|---|---|---|
| Methylene blue | g | 0.01 |
| Poloxamer 338 (Kolliphor ® P338) | g | 10.00 |
| Lecithin | g | 1.50 |
| Sodium oleate | g | 0.02 |
| Cetylpyridinium chloride | g | 0.01 |
| Oleic alcohol | g | 3.00 |
| Purified water | ml | q.b. a 100 |

Lecithin (15.0 g), sodium oleate (0.20 g), cetylpyridinium chloride (0.1 g) and oleic alcohol (30.0 g) are added to 700 ml of purified water in a dissolutor equipped with mechanical stirring. Stirring is maintained until a homogeneous solution is obtained.

The stirring rate is set at 800 rev/min, and Kolliphor® P338 (100.0 g) is added under stirring. The mixture obtained is filtered on high porosity filter paper, and the volume brought to the final value (1000 ml) with purified water. Methylene blue (0.12 g, equivalent to about 0.1 g of anhydrous substance) is added. The mixture is maintained under stirring until complete dissolution of the methylene blue.

Example 8

| Component | Unit of Measure | Amount for 100 ml |
|---|---|---|
| Methylene blue | g | 0.05 |
| Sodium dihydrogen phosphate, anhydrous | g | 6.95 |
| Dibasic sodium phosphate, anhydrous | g | 1.59 |
| Sodium hydroxide | g | 0.06 |
| Caprylocaproyl macrogol-8 glycerides (Labrasol ®) | g | 10.00 |
| Medium chain triglycerides (Labrafac ™ Lipophile WL1349) | g | 2.00 |
| Diethylene glycol monoethyl ether (Transcutol ®) | g | 5.00 |
| Carbomer 980 (Carbopol ® 980) | g | 1.50 |
| Sodium benzoate | g | 0.10 |
| Methyl p-hydroxybenzoate | g | 0.10 |
| Purified water | ml | q.b. a 100 |

Sodium dihydrogen phosphate anhydrous (69.5 g), dibasic sodium phosphate, anhydrous (15.9 g), sodium hydroxide (0.6 g), Transcutol® (50.0 g), Labrasol® (100.0 g), Labrafac™ Lipophile WL1349 (20.0 g), sodium benzoate (1.0 g) and methyl p-hydroxybenzoate (1.0 g) are added to 750 ml of purified water in a dissolutor equipped with mechanical stirring. Stirring is maintained until a homogeneous solution is obtained.

The stirring rate is set at 800 rev/min, and Carbopol® 980 (15.0 g) is added under stirring. The mixture obtained is filtered on high porosity filter paper, and the volume brought to the final value (1000 ml) with purified water. Methylene blue (0.6 g, equivalent to about 0.5 g of anhydrous substance) is added. The mixture is maintained under stirring until complete dissolution of the methylene blue. This composition has evacuative and staining properties, and can be used for the evacuation and the cleansing of the sigma and the rectum in preparation to sigmoidoscopy and rectoscopy Example 9

| Component | Unit of Measure | Amount for 100 ml |
|---|---|---|
| Indigo carmine | g | 0.04 |
| Sodium lauryl sulfate | g | 5.00 |
| Diethylene glycol monoethyl ether (Transcutol ®) | g | 5.00 |
| Sodium sulfate | g | 1.10 |
| Hydroxypropyl cellulose | g | 1.00 |
| Potassium sorbate | g | 0.20 |
| Methyl p-hydroxybenzoate | g | 0.10 |
| Propil p-hydroxybenzoate | g | 0.05 |
| Isopropil myristate | g | 1.00 |
| Purified water | ml | q.b. a 100 |

Sodium lauryl sulfate (50.0 g), Transcutol® (50.0 g), sodium sulfate (11.0 g), potassium sorbate (2.0 g), methyl p-hydroxybenzoate (1.0 g), propyl p-hydroxybenzoate (0.5 g) and isopropyl myristate (10.0 g) are added to 800 ml of purified water in a dissolutor equipped with mechanical stirring. Stirring is maintained until a homogeneous solution is obtained.

The stirring rate is set at 800 rev/min, and hydroxypropyl cellulose (10.0 g) is added under stirring. The volume is brought to the final value (1000 ml) with purified water. Indigo carmine (0.588 g, equivalent to about 0.400 g of anhydrous substance) is added. The mixture is maintained under stirring until complete dissolution of the indigo carmine.

Example 10

| Component | Unit of Measure | Amount for 100 ml |
|---|---|---|
| Methylene blue | g | 0.04 |
| Polyethylene glycol 20 sorbitan monolaurate (Tween ® 20) | g | 5.00 |
| Polyethylene glycol 6000 (PEG 6000) | g | 2.00 |
| Benzalkonium chloride | g | 0.01 |
| Castor oil | g | 0.50 |
| Purified water | ml | q.b. a 100 |

Tween® 20 (50.0 g), benzalkonium chloride (0.1 g), and castor oil (5.00 g) are added to 850 ml of purified water in a dissolutor equipped with mechanical stirring. Stirring is maintained until a homogeneous solution is obtained.

The stirring rate is set at 800 rev/min, and PEG 6000 (20.0 g) is added under stirring. The volume is brought to the final value (1000 ml) with purified water. Methylene blue (0.5 g, equivalent to about 0.4 g of anhydrous substance) is added. The mixture is maintained under stirring until complete dissolution of the methylene blue.

Example 11

| Component | Unit of Measure | Amount for 100 ml |
|---|---|---|
| Methylene blue | g | 0.02 |
| Poloxamer 407 (Kolliphor P407) | g | 12.0 |
| 30% simethicone emulsion | g | 0.10 |
| Ascorbyl Palmitate | g | 0.05 |
| Polyoxyl-15 hydroxystearate (Solutol ®$^{HS15}$) | g | 5.00 |
| Medium chain triglycerides (Labrafac ® Lipophile WL1349) | g | 1.00 |
| Diethylene glycol monoethyl ether (Transcutol ®) | g | 5.00 |
| Hydroxypropyl Cellulose | g | 3.00 |
| Sodium benzoate | g | 0.10 |
| Methyl p-hydroxybenzoate | g | 0.10 |
| Purified water | ml | q.b. a 100 |

Medium chain triglycerides (10.0 g) and polyoxyl-15-hydroxystearate (50 g) are hot mixed in a suitable dissolutor; 150 ml of purified water are then added, under stirring (mixture A).

Then, a different dissolutor is charged with 700 ml of purified water under stirring, to which 30% simethicone emulsion (1.0 g), Kolliphor p407 (120 g), hydroxypropyl cellulose (30 g) and sodium benzoate (1.0 g) are added, and stirring is maintained until a homogeneous mixture is obtained (Mixture B). Mixture A is added under stirring to Mixture B, and stirring is maintained until a homogeneous mixture is obtained (Mixture C).

A dissolutor is charged with dietilen diethylene glycol monoethyl ether (50.0 g); it is placed under stirring at room temperature and methyl-p-hydroxybenzoate (1.0 g) and ascorbyl palmitate (0.5 g) are added, keeping under stirring until a clear solution is obtained (Mixture D).

Mixture D is added to Mixture C in the dissolutor, keeping under stirring until a clear solution is obtained (Mixture E). Finally, a different dissolutor is charged with purified water (100 ml) and placed under stirring; methylene blue (0.2 g) is then added under stirring until a clear solution is obtained (Mixture F). This mixture F is added to Mixture E under stirring, and it is brought to final volume (I liter) with purified water.

The invention claimed is:

1. A method of an endoscopic procedure for the identification of pathological and/or non-pathological forms of the mucosa of the sigmoid colon and/or rectum of a subject, the method consisting of (a) rectally administering a liquid composition to the sigmoid colon and/or rectum of a subject undergoing an endoscopic procedure and (b) evaluating the mucosa of said sigmoid colon and/or rectum of said subject, wherein the liquid composition is formulated as an enema and is in the form of an emulsion or microemulsion comprising at least one dye, at least one emulsifier, at least one inverse thermosensitive polymer with a critical gelation temperature below 45° C. and at least one physiologically acceptable excipient and wherein the rectal administration of the liquid composition brings the liquid composition into contact with the mucosal walls of the sigmoid colon and/or rectum of the subject, thereby cleansing and staining the surface layer of the mucosal walls of the sigmoid colon and/or rectum of the subject.

2. The method according to claim 1, wherein said endoscopic procedure of said sigmoid colon and/or rectum is an anoscopy, a proctoscopy, a rectoscopy and/or a sigmoidoscopy.

3. The method according to claim 1, wherein said at least one dye is selected from the group comprising vital dyes, non-vital dyes, reactive dyes, or mixtures thereof.

4. The method according to claim 3, wherein said at least one dye is selected from methylene blue, toluidine blue, Lugol's solution, cresyl violet, indigo carmine, Congo red, phenol red, fluorescein, or mixtures thereof.

5. The method according to claim 4, wherein said east one dye is methylene blue, indigo carmine, or a mixture thereof.

6. The method according to claim 1, wherein said at least one emulsifier is a non-ionic emulsifier, an ionic emulsifier, a natural emulsifier, or mixtures thereof.

7. The method according to claim 6, wherein said at least one emulsifier is a non-ionic emulsifier.

8. The method according to claim 7, wherein said non-ionic emulsifier is selected from poloxamer 407, caprylocaproyl macrogol-8 glycerides, polisorbate 80, PEG-40 stearate, propylene glycol monocaprylate, lauroyl macrogol-32 glycerides, polyoxyl-15-hydroxystearate, or mixtures thereof.

9. The method according to claim 1, wherein said at least one inverse thermosensitive polymer is a poloxamer.

10. The method according to claim 9, wherein said poloxamer is selected from poloxamer 124, poloxamer 188, poloxamer 237, poloxamer 338, poloxamer 407, or mixtures thereof.

11. The method according to claim 10, wherein said poloxamer is selected from poloxamer 188, poloxamer 407, or a mixture thereof.

12. The method according to claim 1, wherein said liquid composition comprises at least one viscosity modifying agent.

13. The method according to claim 12, wherein said at least one viscosity modifying agent is selected from hydroxypropyl cellulose, hydroxypropylmethyl cellulose, hydroxyethyl cellulose, PEG 6000, a carbomer, a carboxyvinyl polymer, polyvinylpyrrolidone, or a mixture thereof.

14. The method according to claim 1, wherein said emulsion or microemulsion is an oil-in-water, water-in-oil, oil-in-water-in-oil or water-in-oil-in-water.

15. The method according to claim 1, wherein said pathological and/or non-pathological forms of the mucosa of said sigmoid colon and/or rectum of said subject are selected from inflammatory lesions, ulcers, polyps, pseudo-polyps, flat polyps, hyperplastic polyps, tightened lesions, adenomas, pre-neoplastic formations, neoplastic formations, tumors, carcinoma or combinations thereof.

* * * * *